(12) United States Patent
Leung et al.

(10) Patent No.: US 10,918,275 B2
(45) Date of Patent: Feb. 16, 2021

(54) OPTICAL TEXTURE ANALYSIS OF THE INNER RETINA

(71) Applicant: The Chinese University of Hong Kong, Hong Kong (CN)

(72) Inventors: Kai Shun Christopher Leung, Hong Hong (CN); Ka Ngai Alexander Lam, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 153 days.

(21) Appl. No.: 16/159,476

(22) Filed: Oct. 12, 2018

(65) Prior Publication Data

US 2019/0110681 A1    Apr. 18, 2019

Related U.S. Application Data

(60) Provisional application No. 62/571,559, filed on Oct. 12, 2017.

(51) Int. Cl.
| | | |
|---|---|---|
| *A61B 3/14* | (2006.01) | |
| *A61B 3/12* | (2006.01) | |
| *G06T 5/00* | (2006.01) | |
| *A61B 3/10* | (2006.01) | |
| *A61B 5/00* | (2006.01) | |
| *G06T 7/00* | (2017.01) | |

(52) U.S. Cl.
CPC ............... *A61B 3/12* (2013.01); *A61B 3/102* (2013.01); *A61B 3/14* (2013.01); *G06T 5/002* (2013.01); *A61B 5/0066* (2013.01); *G06T 7/0012* (2013.01); *G06T 2207/10101* (2013.01); *G06T 2207/30041* (2013.01)

(58) Field of Classification Search
CPC ...... A61B 3/102; A61B 3/10; G01B 9/02083; G01B 9/02091; G01N 21/47; G01N 21/4795; G01N 2021/4709
USPC ........................................ 351/205, 206, 246
See application file for complete search history.

(56) References Cited

U.S. PATENT DOCUMENTS

| 8,721,077 B2 | 5/2014 | Vermeer et al. | |
|---|---|---|---|
| 2011/0176716 A1* | 7/2011 | Kim ....................... | G06T 3/0075 382/131 |
| 2015/0124216 A1* | 5/2015 | Abramoff ............ | A61B 3/0025 351/206 |

* cited by examiner

*Primary Examiner* — Mahidere S Sahle
(74) *Attorney, Agent, or Firm* — Kilpatrick Townsend & Stockton LLP

(57) ABSTRACT

Optical texture analysis of the inner retina, including the retinal nerve fiber layer (RNFL), ganglion cell layer (GCL), or inner plexiform layer (IPL), or a combination of these layers, can be used to detect and quantify RNFL/GCL/IPL abnormalities. From a set of scans of a retina, anterior and posterior boundaries of an inner retinal layer of interest can be determined. Optical density measurements at specific locations on the retina and depths within the layer of interest can be extracted from the scans. From these measurements, a set of optical texture signature values corresponding to different locations can be computed, where the optical texture signature value for a given location provides information about a tissue composition of the inner retinal layer at that location. The texture signature values can provide a topographical map of a retinal layer, which can facilitate detection and quantification of abnormalities.

13 Claims, 7 Drawing Sheets
(5 of 7 Drawing Sheet(s) Filed in Color)

OPTICAL TEXTURE ANALYSIS OF THE INNER RETINA

CROSS-REFERENCE TO RELATED APPLICATION

This application claims the benefit of U.S. Provisional Application No. 62/571,559, filed Oct. 12, 2017, the disclosure of which is incorporated herein by reference in its entirety.

BACKGROUND

The present disclosure relates generally to imaging of the retina and in particular to optical texture analysis of the inner retina.

The retinal nerve fiber layer (RNFL), ganglion cell layer (GCL), inner plexiform layer (IPL) are three inner retinal layers containing the axon fibers, soma, and dendrites of retinal ganglion cells (RGCs), respectively. Identifying RNFL, GCL, IPL abnormalities is pivotal to the detection and monitoring of optic nerve disorders as all forms of optic neuropathies are characterized by degeneration of RGCs. While red-free photography has been the standard to visualize RNFL abnormalities for decades, cross-sectional digital imaging instruments, such as optical coherence tomography (OCT), have considerably improved the sensitivity for detection of RNFL abnormalities. In addition to the evaluation of the RNFL, OCT also allows examination of the GCL and IPL. OCT measurements of GCL and IPL thicknesses have been shown to be useful to discriminate patients with glaucomatous optic neuropathy from normal individuals.

The current standard for assessment of RNFL/GCL/IPL abnormalities is predicated on the analysis of RNFL/GCL/IPL thickness profiles. For example, the circumpapillary RNFL thickness profile (i.e. RNFL thickness measurements obtained from the 3.46 mm diameter circle) is often used in clinical practice for detection of RNFL abnormalities. With the advent of Fourier-domain optical coherence tomography, RNFL/GCL/IPL thickness assessment extends to a region of interest. For example, the spectral-domain OCT from Carl Zeiss Meditec (Cirrus HD-OCT) analyzes the RNFL thicknesses in a 6×6 mm$^2$ parapapillary region, and the ganglion cell inner plexiform layer (GCIPL) thicknesses in a 6×6 mm$^2$ macular region. RNFL/GCL/IPL abnormalities are displayed using RNFL/GCL/IPL thickness deviation maps, which are generated by pixel-by-pixel comparison of RNFL thicknesses with the normative database of the OCT instrument (i.e., RNFL/GCL/IPL thickness values collected from healthy individuals). FIGS. 1A-1F illustrate an example of a circumpapillary RNFL thickness profile (expressed in μm) for a normal eye and a glaucomatous eye. FIGS. 1A and 1B show optic disc photographs of a normal eye (FIG. 1A) and a glaucomatous eye (FIG. 1B). FIGS. 1C and 1D show the corresponding RNFL pixel deviation maps for the photographs of FIGS. 1A and 1B, respectively. Pixels encoded in red signify abnormal RNFL thickness, typically defined as thickness below the lower 99th percentile of the normative data. FIGS. 1E and 1F show corresponding circumpapillary RNFL thickness profiles in a clock-hour format for the RNFL pixel deviation maps of FIGS. 1C and 1D, respectively. Red sectors signify abnormal RNFL thickness. In this example, false positive detection of RNFL thickness abnormalities occurs in the normal eye.

Although the application of RNFL/GCL/IPL thickness deviation maps represents the conventional standard for detection of RNFL/GCL/IPL abnormalities, their diagnostic performance is often impaired in eyes with myopia, which is a prevalent condition in many Asian countries. Discerning different degrees of RNFL/GCL/IPL abnormality is also compromised in the RNFL/GCL/IPL thickness deviation map in advanced optic neuropathies when most or all of the RNFL/GCL/IPL thickness deviation maps would be encoded in red.

SUMMARY

Certain embodiments of the present invention relate to using optical texture analysis of the RNFL/GCL/IPL to visualize and quantify topographic RNFL/GCL/IPL abnormalities in an area covering both the parapapillary region and the macula. Optical texture analysis of the RNFL/GCL/IPL, e.g., as described herein, can be used to evaluate abnormalities in the RNFL, GCL, and/or IPL without the need of normative databases. This can improve the sensitivity and specificity for detection of RNFL/GCL/IPL abnormalities compared with conventional approaches for analysis of the RNFL/GCL/IPL thickness and can allow different levels of optic nerve damage to be discerned in patients with advanced glaucoma (or other eye diseases that may cause optic neuropathy), which is generally not possible with conventional clinical tools.

Some embodiments of the present invention use digital optical imaging instruments, such as optical coherence tomography (OCT), to measure the optical density of the retinal layers. In OCT images, the intensities of particular pixels are associated with the tissue constituents of the individual retinal layers. For instance, axonal fibers generally have high optical density whereas soma and dendritic structures generally have low optical density. Multiple cross-sectional retinal images covering the parapapillary area and the macula are captured and analyzed to construct an RNFL/GCL/IPL optical texture analysis map. The map displays a part of the retina (e.g. 6×6 mm$^2$), or the entire retina (an area with a diameter of 30-40 mm). Each pixel location of the optical texture analysis map corresponds to a location on the retina and encompasses a set of optical density data for that location at different scan depths. Optical density measurements corresponding to the RNFL/GCL/IPL are extracted from images of specific retinal locations ($P_{z,xy}$, where x corresponds to the A-scan location, y corresponds to the B-scan location, and z corresponds to the scan depth of the pixel in A-scan) and used to compute an optical texture signature value ($S_{xy}$) at that particular retinal location. In some embodiments, the computation involves normalization of $P_{z,xy}$ with a reference optical density ($P_{ref}$); non-linear transformation of $P_{z,xy}/P_{ref}$ normalization of the summation of $P_{z,xy}/P_{ref}$ with a pre-defined constant α (i.e. $\Sigma(P_{z,xy}/P_{ref})/\alpha$); and non-linear transformation of $\Sigma(P_{z,xy}/P_{ref})/\alpha$. The optical texture signature value $S_{xy}$ can be understood as representing optical density of the relevant retinal layer (RNFL, GCL, and/or IPL) at a particular location on the retina. Since optical density is affected by tissue composition, $S_{xy}$ indirectly provides information about the tissue composition at a particular retinal location. Specific examples of computing $S_{xy}$ are described below.

The RNFL/GCL/IPL optical texture analysis map is then generated to display $S_{xy}$ at individual retinal locations. Normal RNFL/GCL/IPL texture signatures exhibit specific patterns across the retina, including higher $S_{xy}$ values over the inferotemporal and the superotemporal sectors of the optic nerve head and the papillomacular bundles (i.e. superotemporal and inferotemporal sectors of the macula) compared with the nasal retina. RNFL/GCL/IPL abnormalities can therefore be identified when these specific patterns are breached. In some embodiments, deep learning techniques are applied for recognition of normal versus abnormal RNFL/GCL/IPL texture signatures. Since the patterns of optical texture signatures in eyes with optic nerve disorders are intuitively different from normal eyes, normative databases are not necessary to detect RNFL/GCL/IPL abnormalities.

Some embodiments may include quantification of the degree of RNFL/GCL/IPL abnormalities in the form of optical texture signature measurement at a particular retinal location, or as an averaged optical texture signature measurement of a region of the retina or the entire retina.

In some embodiments, the optical texture signature values of the RNFL/GCL/IPL are quantified in the form of probability scores, indicating likelihood that the optical texture signature values of individual retinal locations, a region of the retina, or the entire retina are abnormal.

Other embodiments may include prediction of visual sensitivity at specific locations of the retina, generating a visual sensitivity map or visual field of an eye.

These and other embodiments may facilitate any or all of: (1) visualization of the topographic distributions of the optical texture of an inner retinal layer (e.g., RNFL, GCL, and/or IPL) via non-linear transformations of normalized optical density measurements of the layer; (2) quantification of abnormalities in an inner retinal layer, which can be useful for detection and monitoring of optic nerve disorders; and/or (3) prediction of visual sensitivities at specific locations of the retina.

The following detailed description, together with the accompanying drawings, will provide a better understanding of the nature and advantages of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows a flowchart of an analysis process, and FIGS. 2B-2F shows example images illustrating various aspects of the process shown in FIG. 2A.

DETAILED DESCRIPTION

Certain embodiments of the present invention relate to using optical texture analysis of the RNFL/GCL/IPL to visualize and quantify topographic RNFL/GCL/IPL abnormalities in an area covering both the parapapillary region and the macula. Described herein are examples of methods for (1) visualization of the topographic distributions of the optical texture signature of the RNFL/GCL/IPL; (2) quantification of RNFL/GCL/IPL optical texture signature for detection and monitoring of RNFL/GCL/IPL abnormalities; and (3) prediction of visual sensitivities at specific locations of the retina. (As used herein, "RNFL/GCL/IPL" includes any one of these three inner retinal layers or any combination of two or more of them considered together.)

Figure 1A:
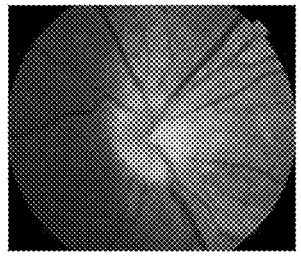
FIGS. 1A-1F illustrate a conventional assessment of RNFL abnormalities, in which detection of abnormalities is predicated on the analysis of RNFL thickness profiles.
Figure 1B:
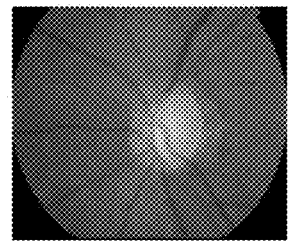
Figure 1C:
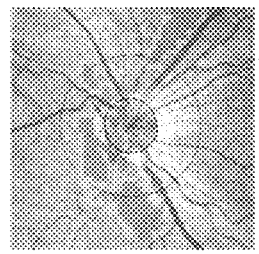
Figure 1D:
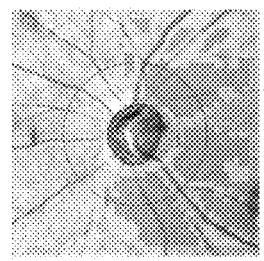
Figure 1E:
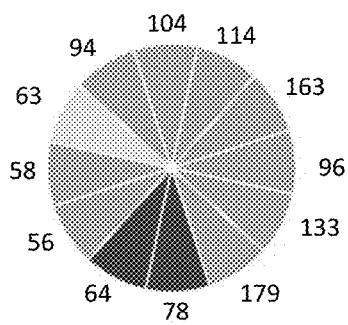
Figure 1F:
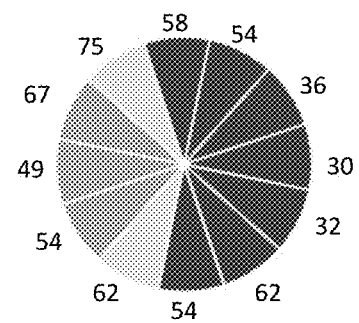
Figure 2A:
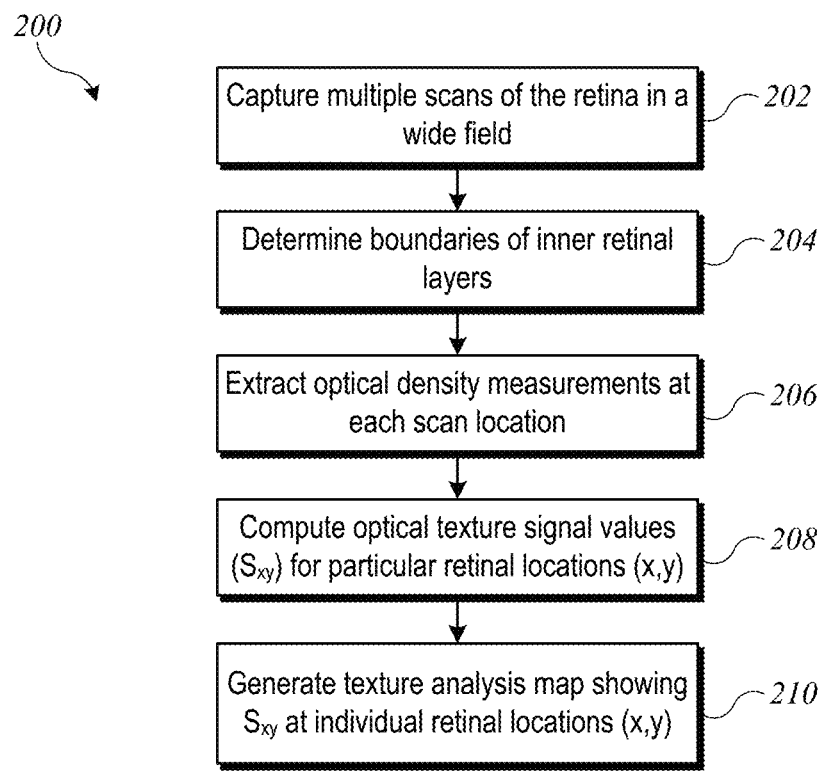
FIGS. 2A-2F illustrate a method for generating an optical texture signature of an inner retina layer according to an embodiment of the present invention.

FIG. 2A is a flow diagram of a process 200 for computing an optical texture analysis map according to an embodiment of the present invention. Process 200 can be implemented, e.g., in a computer program executed on an appropriate computer system, which can be a general-purpose system or a purpose-built system as desired. Process 200 includes extracting three-dimensional optical density measurements from images of the retina obtained using a digital imaging instrument, such as optical coherence tomography (OCT); transforming the three-dimensional optical density measurements of a specific inner retinal layer (i.e. RNFL, GCL, IPL, or any combination of the above) at a specific retinal location (x, y) to optical texture signature values ($S_{xy}$) of that particular layer at that particular retinal location; and generating a topographic display of the computed optical texture signature values of the inner retinal layer(s).

Figure 2B:
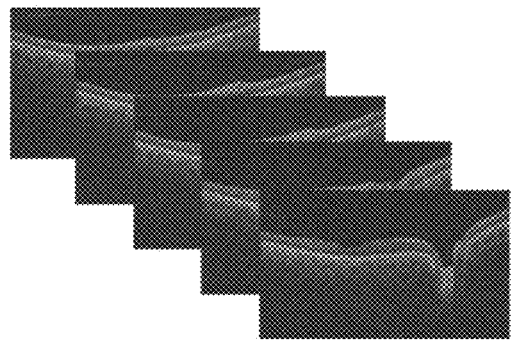

More specifically, at block 202, multiple scans of the retina in a wide field are captured. For example, conventional optical coherence tomography (OCT) may be used. In OCT, an "A-scan" is captured based on the time-delay of light reflected from each optical interface as a pencil of light enters the eye. Repeated A-scans across the retina can be used to reconstruct a cross-section of a plane through the retina; such a cross section is referred to as a "B-scan." It is generally desirable to capture multiple B-scans of the retina, providing cross-sections through different portions of the retina. In some embodiments, the wide field (e.g., 12×9 mm$^2$) covers the macula and the optic nerve head. FIG. 2B shows sample B-scan images that may be used.

Figure 2C:
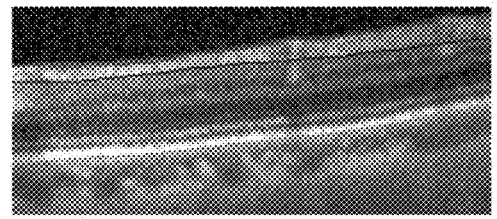

At block 204, boundaries of the inner retinal layers are determined. The inner retinal layers in this example include RNFL, GCL, and IPL. In some embodiments, determination of boundaries is achieved by analyzing specific threshold transitions of the optical density in the individual A-scans. FIG. 2C shows a sample cross-sectional image with anterior and posterior boundaries of the RNFL outlined in red and blue, respectively.

Figure 2D:
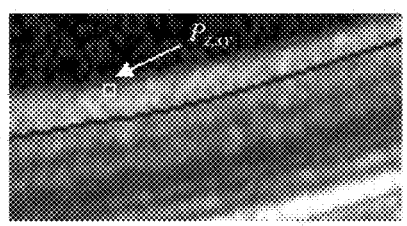

At block 206, optical density measurements at specific retinal locations are extracted. The optical density measurements can be extracted for multiple retinal locations within a layer of interest, such as the RNFL, based on the boundaries determined at block 204. FIG. 2D shows a sample scan location having optical density $P_{z,x,y}$, where z corresponds to the scan depth of the A-scan, x corresponds to the A-scan location, and y corresponds to the B-scan location. (The two-dimensional coordinates (x, y) correspond to a particular location on the surface of the retina, also referred to herein as a retinal location.)

Figure 2E:
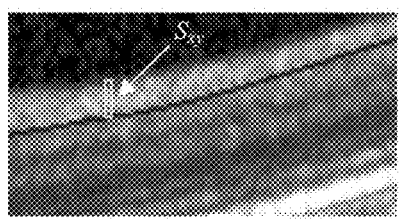

At block 208, an optical texture signal value ($S_{xy}$) is computed for particular retinal locations using the optical density measurements $P_{z,x,y}$ extracted at block 206. In some embodiments, $S_{xy}$ is computed for all available retinal locations (x, y), which may be limited based on the resolution of the scans. $S_{xy}$ can be computed separately for different inner retinal layers (e.g., RNFL, GCL, IPL) or computed for two or more inner retinal layers considered together. As shown in FIG. 2E, the optical texture signal value $S_{xy}$ can provide information about the tissue composition of a retinal layer of interest at a particular retinal location (x, y). In some embodiments, $S_{xy}$ is computed in a manner that accounts for imaging artifacts such as noise and gamma correction. For example, the optical texture signal value $S_{xy}$ of a particular retinal location (x, y) can be computed using the following equation:

$$S_{xy} = \left\{ \sum_{z=b_{1,xy}}^{b_{2,xy}} \left( \frac{P_{z,xy}}{P_{ref}} \right)^{\gamma_1} / \alpha \right\}^{\frac{1}{\gamma_2}} \quad (1)$$

where $b_{1,xy}$ and $b_{2,xy}$ correspond to the anterior and posterior boundaries, respectively, of the retinal layer of interest (e.g., the RNFL) at the retinal location (x, y); $P_{ref}$ corresponds to a reference optical density value for normalization calculated with reference to a global or local signal-to-noise ratio; $\gamma_1$ corresponds to a gamma value for application of a gamma transformation function; $\gamma_2$ corresponds to a gamma value for application of a gamma correction function; and a corresponds to a predefined constant proportional to the peak tissue thickness of the retinal layer of interest.

In this example, normalization of the optical density measurements is applied relative to a reference optical density value ($P_{ref}$) calculated with the overall (global) signal-to-noise ratio or local signal-to-noise ratios of individual B-scans before computation of the optical texture signature values. Various references can be used. For example, $P_{ref}$ can be the mean, median, or maximum optical density value of any of: (a) the outer nuclear layer; (b) the inner segment and outer segment junction; (c) the retinal pigment epithelium; (d) the choroidal layer; or (e) a combination of some or all of (a)-(d).

Nonlinear transformation, in this case gamma transformation ($p^{\gamma}$), may be applied to the normalized optical density measurements of a specific retinal location prior to summation, and a further non-linear transformation such as gamma correction ($p^{1/\gamma}$) may be applied to the computed summation of the normalized, gamma transformed optical density measurements.

Those skilled in the art will appreciate that different definitions of $S_{xy}$ may be used. For instance, in Eq. (1), the individual optical density measurements $P_{z,xy}$ are normalized and gamma-transformed prior to summing over depths z. In other embodiments, normalization and/or gamma transformation can be applied after summing. Further, other non-linear transformations can be applied in addition to or instead of gamma transformation and/or gamma correction, including power functions, exponential functions, or logarithmic functions.

Figure 2F:
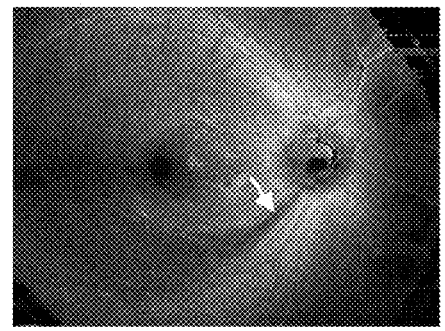

At block 210, a displayable texture analysis map is generated. As used herein, a displayable texture analysis map can include any representation of $S_{xy}$ for a particular retinal layer of interest as a function of retinal location (x, y). Examples include: color (or grayscale) maps where the color (or intensity) at a particular coordinate represents $S_{xy}$, three-dimensional rendering (e.g., topographic maps), and so on. FIG. 2F shows an example of a grayscale texture analysis map that can be generated according to an embodiment of the present invention. The displayable texture analysis map may be presented to a user (e.g., an ophthalmologist or other medical professional) in various ways. For example, a texture analysis map can be displayed on a computer monitor or other display device, and/or printed onto paper or other media. In some embodiments, the data underlying or representing the displayable texture analysis map can be stored as a computer-readable file, which can be retrieved for subsequent transmission and/or display and/or transmission.

In some embodiments, displayable texture analysis maps produced by process 200 can be used to diagnose disorders affecting the retina. For example, normal RNFL/GCL/IPL texture signatures exhibit specific patterns, including higher $S_{xy}$ values over the inferotemporal and superotemporal sectors of the optic nerve head and the papillomacular bundles (i.e., superotemporal and inferotemporal sectors of the macula) compared with the nasal retina. RNFL/GCL/IPL abnormalities can therefore be identified based on deviation from these specific patterns. For example, the texture analysis map of FIG. 2F demonstrates an inferotemporal RNFL defect, indicated by the white arrow.

In some embodiments, diagnosis based on texture analysis maps can be partially or fully automated, e.g., using machine learning techniques. For example, a training data set can be generated by performing process 200 for a large number of eyes that are known to be healthy or abnormal (e.g., glaucomatous with varying degrees of RNFL/GCL/IPL damage). The optical texture signature maps generated by process 200 and the known condition of the eyes can be provided as inputs to a training phase of a machine learning algorithm (e.g., a deep neural network or other deep learning algorithm), and conventional techniques can be used to train the algorithm to identify patterns associated with a particular condition. In some embodiments, the output can be a probabilistic assessment indicating the likelihood that a particular abnormal condition is or is not present. In some embodiments, a single machine learning algorithm can be trained to recognize multiple different abnormal conditions (as well as healthy eyes) and assign probabilities to each.

In some embodiments, progressive generalized and localized changes in retinal layers can be monitored, e.g., by repeating process 200 for the same patient at intervals across a period of time, longitudinally normalizing the optical texture signature values from different scans, and performing event-based or trend-based analysis on the normalized results.

Figure 3:
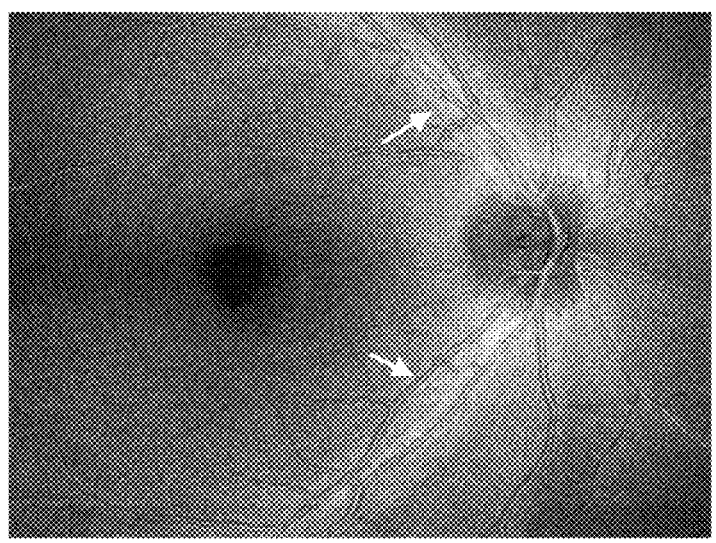
FIG. 3 shows an example of an optical texture analysis map of a normal eye with optical texture values computed from OCT scans imaged from a healthy individual according to an embodiment of the present invention.

FIG. 3 illustrates an example of a topographic display of an RNFL optical texture analysis map of a normal eye. The white arrows indicate high optical texture signature values over the inferotemporal and the superotemporal sectors of the optic nerve head. The map is composed of 512×256 pixels (12×9 mm$^2$) with optical density measurements obtained from a swept-source OCT. The RNFL optical texture analysis map is able to reveal additional features of the RNFL that are missed by conventional RNFL thickness maps and/or RNFL thickness deviation maps. Examples of such features include the trajectories of the papillomacular bundles, the axonal fibers at the temporal macula, and the interface between the nerve fibers and the retinal blood vessels.

Figure 4A:
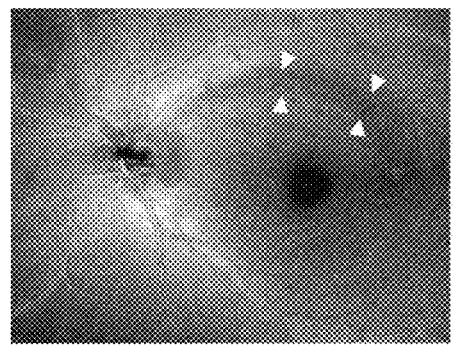
FIGS. 4A-4D show a comparison of conventional methods (RNFL thickness map and RNFL thickness deviation map) and a method according to an embodiment of the present invention.

FIGS. 4A-4D illustrate a comparison between techniques described herein and conventional techniques for assessment of RNFL abnormalities. FIG. 4A shows an example of a topographic display of the optical texture signature of the RNFL (i.e. an RNFL optical texture analysis map generated according to an embodiment of the present invention) of an eye with early glaucoma. The white arrowheads indicate an RNFL abnormality, specifically, a reduced optical texture signal at the superotemporal sector of the optic disc. Abnormality is also observed over the superior rim of the macula.

Figure 4B:
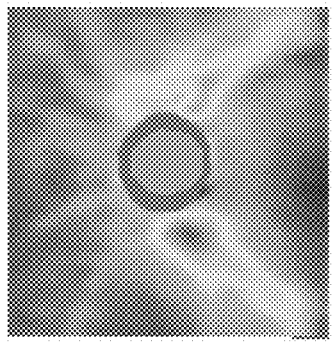
Figure 4C:
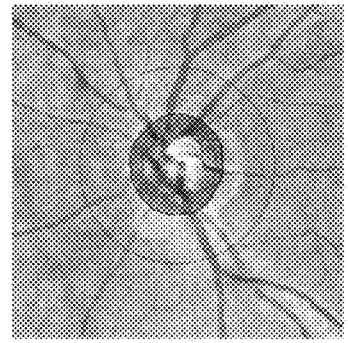

FIG. 4B shows an RNFL thickness map generated for the same eye as FIG. 4A using conventional techniques, and FIG. 4C shows a corresponding RNFL thickness deviation map, also generated using conventional techniques. In this example, the conventional technique fails to detect the RNFL abnormalities, as no portion of the RNFL thickness map is coded red.

Figure 4D:
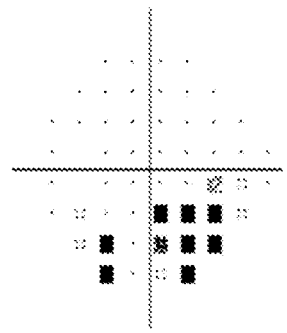

FIG. 4D shows a result of a visual field examination for the same eye, in the form of a conventional visual field pattern deviation plot. This plot confirms an inferonasal visual field defect corresponding to the RNFL abnormality observed in the RNFL optical texture analysis map of FIG. 4A.

As this example illustrates, embodiments of the present invention may be capable of detecting abnormalities indicative of early glaucoma that may be missed using conventional techniques.

Figure 5A:
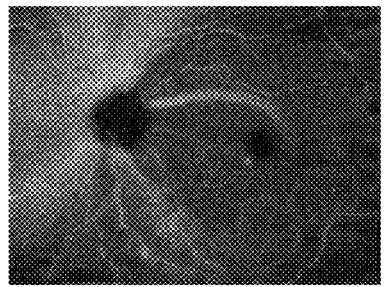
FIGS. 5A-5D show results of analysis according to an embodiment of the present invention for eyes with advanced glaucoma and different levels of RNFL damage.
Figure 5B:
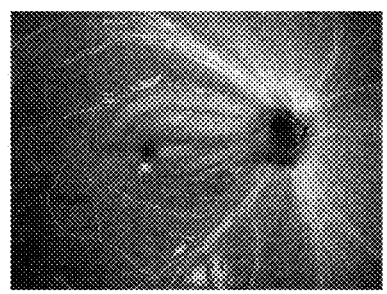
Figure 5C:
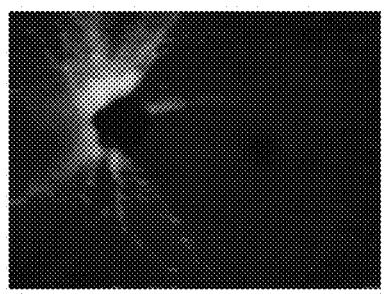
Figure 5D:
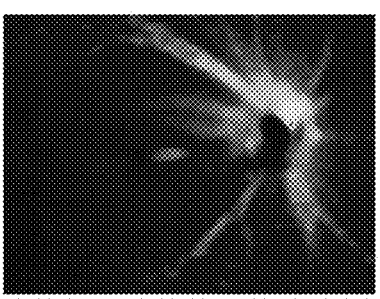

FIGS. 5A-5D show another example comparing techniques described herein and conventional techniques, in this case for eyes with advanced glaucoma. FIGS. 5A and 5B show RNFL optical texture analysis maps generated according to an embodiment of the present invention, for two different eyes with advanced glaucoma. The RNFL optical texture analysis maps show that the two eyes exhibit different degrees of RNFL damage, e.g., in the area over the papillomacular bundle. For comparison, FIGS. 5C and 5D show color-coded RNFL thickness maps generated using conventional techniques for the same eyes as FIGS. 5A and 5B, respectively. The conventional optical coherence tomography RNFL thickness analysis fails to discern different levels of RNFL damage; in other words, false color coding of RNFL thickness cannot reveal the differences in the degree of RNFL damage. As this example illustrates, embodiments of the present invention may be capable of more accurately detecting specific levels of RNFL damage in a glaucomatous eye.

Figure 6:
FIG. 6 shows a topographic display of the optical texture signature values encoded with reference to a color-coding scale according to an embodiment of the present invention.

In some embodiments, the optical texture signature values may be used to quantify the degree of RNFL abnormalities. FIG. 6 shows an example of a topographic display of optical texture signature values for an eye, encoded using a color-coding scale according to an embodiment of the present invention. The optical texture signature value is directly proportional to the degree of RNFL abnormalities. A lower optical texture signature value is associated with a higher degree of RNFL damage. The optical texture signature values can be reported at the individual pixels of the RNFL optical texture analysis map, or as a global value averaged over the individual optical texture signature values of different retinal locations with or without additional weighting of the values at the macula, or as regional values at specific areas around the optic disc or at the macula.

In some embodiments, the optical texture signature values of the RNFL/GCL/IPL may be quantified in the form of probability scores, indicating how likely the optical texture signature measurements of individual pixel locations, a region of the retina, or the entire retina are abnormal. Particular algorithms for generating probability scores may be developed, e.g., using machine learning techniques, such as deep neural networks, deep learning, or the like.

In some embodiments, the optical texture signature values of a pixel or an area of the BNFL optical texture analysis map can be converted to a visual sensitivity value (e.g. visual field expressed in dB) of that particular pixel or area. The conversion can be based on a location specific structure function association derived from linear or non-linear regression analysis between optical texture signature values and visual sensitivity measured from a standard automated white-on-white perimetry.

Embodiments described herein can be implemented using an imaging system communicably coupled to a computer system. The imaging system can be, for example, an OCT system of conventional or other design that produces images via a scanning process. Images (also referred to as scans) captured by the imaging system can be stored locally at the imaging system, stored on removable storage media, and/or transmitted via a wired or wireless communication interface to a computer system for analysis.

The computer system can include a processor capable of executing program code implementing a method as described herein to analyze image data provided by the imaging system. The computer system can receive and/or read the image data. For instance, if the imaging system stores the data locally (e.g., on a hard drive), a computer system local to the imaging system may be able to read the data from the local storage medium. If the imaging system stores the data on a removable storage medium, the computer system may have a drive configured to receive and read the storage medium. If the imaging system transmits the data via a communication interface, the computer system may use a compatible interface to receive the data. After receiving and/or reading the image data from the imaging system, the computer system can execute the program code to analyze the data and generate analysis results, e.g., an optical texture analysis map as described above. The computer system can deliver the analysis results to a user (e.g., an optometrist or ophthalmologist). Various delivery methods can be used. For instance, the computer system may include a display device on which results can be presented, a printer allowing results to be presented on paper, and/or the ability to generate and transmit a data file containing the results to another computer system (e.g., via email, secure file transfer protocols, or the like). Those skilled in the art will appreciate that many different system configurations are possible.

Certain embodiments of the present invention relate to methods of visualizing the topography of an optical texture signature of the retinal nerve fiber layer (RNFL), the ganglion cell layer (GCL), the inner plexiform layer (IPL), or a combination of the above of an eye covering the parapapillary area, the macula, and retinal region beyond the parapapillary area and the macula for detection of RNFL and/or GCL and/or IPL abnormalities. The method comprises: collecting pixel-by-pixel optical density measurements of RNFL, GCL and IPL using an optical imaging instrument; computing optical texture signature values in the RNFL, GCL, IPL, or a combination of the above layers at individual retinal locations of interest; and constructing RNFL/GCL/IPL optical texture topographic maps based on the optical texture signature values of individual retinal locations. The optical texture topographic maps can be used, e.g., for visualization and detection of RNFL, GCL, and/or IPL abnormalities.

In some embodiments, the optical texture signature value of an individual retinal location of the RNFL/GCL/IPL optical texture topographic map is calculated from the summation of a non-linear transformation of normalized optical density measurements of individual pixels within the RNFL, the GCL, the IPL, or a combination of the above.

In some embodiments, the optical density measurement of an individual pixel location is normalized with reference to the mean, median or maximum optical density values of the outer nuclear layer, the inner segment and outer segment junction, the retinal pigment epithelium, the choroidal layer, or a combination of the above.

In some embodiments, the non-linear transformation includes a non-linear function such as a power function, an exponential function, or a logarithmic function to non-linearly transform the normalized optical density values of individual pixel locations.

In some embodiments, the summation of non-linear transformations of the optical density measurements of individual pixels within the RNFL, the GCL, and/or the IPL at a given retinal location is further normalized by the maximum possible thickness of the RNFL, the GCL, the IPL, or a combination of the above, at that retinal location.

In some embodiments, the normalized summation of mathematical transformation of the raw optical density values of individual pixels within the RNFL, the GCL, and/or the IPL at a given retinal location can be further transformed by gamma correction.

In some embodiments, the RNFL/GCL/IPL optical texture signature values can be used to quantify the degree of RNFL/GCL/IPL abnormalities for detecting, staging, and monitoring optic neuropathies.

In some embodiments, the RNFL/GCL/IPL optical texture signature values can be used to detect progressive generalized and localized changes of the RNFL/GCL/IPL over time by performing event-based or trend-based analyses of RNFL/GCL/IPL optical texture signature values.

In some embodiments, the method further comprises prediction of visual sensitivities at individual retinal locations from the RNFL/GCL/IPL optical texture signature values.

In some embodiments, the visual sensitivity of a retinal location can be derived from a linear or non-linear relationship between RNFL/GCL/IPL optical texture signature values and visual field sensitivity measured from a standard automated perimetry.

In some embodiments, the method further comprises training and application of artificial intelligence to recognize RNFL/GCL/IPL abnormalities based on RNFL/GCL/IPL optical texture signature values.

In some embodiments, the method further comprises application of deep learning to modify the calculation of RNFL/GCL/IPL optical texture signature values for detection of RNFL/GCL/IPL abnormalities.

While the invention has been described with reference to specific embodiments, those skilled in the art will appreciate that variations and modifications are possible. For instance, while some examples above focus on texture analysis of the RNFL, other embodiments of the present invention can apply similar techniques to other layers of the retina (e.g., GCL and/or IPL), in addition to or instead of RNFL. The invention is also not limited to diagnosing and/or assessing any particular ailment. Any optic neuropathy or other condition that causes abnormal texture in one or more retinal layers (including RNFL, GCL, and/or IPL) may be detected. In some instances, abnormalities in retinal layer texture can be detected and quantified without necessarily being ascribed to any particular cause or condition.

Various features described herein, e.g., methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features described herein may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the invention has been described with respect to specific embodiments, it will be appreciated that the invention is intended to cover all modifications and equivalents within the scope of the following claims.

What is claimed is:

1. A method for analyzing an inner retinal layer, the method comprising:
  capturing a plurality of scans of a retina in a wide field using an image capture device;
  determining, from the scans, anterior and posterior boundaries of an inner retinal layer;
  extracting, from the scans, a set of optical density measurements ($P_{z,xy}$) at each of a plurality of retinal locations (x, y) and a plurality of depths z;
  computing a set of optical texture signature values ($S_{xy}$) from the set of optical density measurements $P_{z,xy}$ for a given retinal location (x, y) at depths z between the anterior and posterior boundaries of the inner retinal layer, wherein the optical texture signature value $S_{xy}$ for a given retinal location (x, y) is computed as:

$$S_{xy} = \left\{ \sum_{z=b_{1,xy}}^{b_{2,xy}} \left(\frac{P_{z,xy}}{P_{ref}}\right)^{\gamma_1} / \alpha \right\}^{\frac{1}{\gamma_2}}$$

wherein $b_{1,xy}$ and $b_{2,xy}$ correspond to anterior and posterior boundaries, respectively, of the inner retinal layer at the retinal location (x, y); $P_{ref}$ corresponds to a reference optical density value for normalization; $\gamma_1$ corresponds to a gamma value for a gamma transformation function; $\gamma_2$ corresponds to a gamma value for a gamma correction function; and $\alpha$ corresponds to a predefined constant proportional to a peak tissue thickness of the inner retinal layer; and
  generating a texture analysis map based on the optical texture signature values $S_{xy}$ at individual retinal locations (x, y).

2. The method of claim 1 wherein the inner retinal layer includes one or more of:
  a retinal nerve fiber layer (RNFL);
  a ganglion cell layer (GCL); or
  an inner plexiform layer (IPL).

3. The method of claim 1 wherein the scans of the retina are captured using an optical coherence tomography (OCT) instrument.

4. The method of claim 1 wherein the scans of the retina cover the parapapillary area, the macula, and at least a portion of an additional retinal region beyond the parapapillary area and the macula.

5. The method of claim 1 wherein determining the anterior and posterior boundaries of the inner retinal layer includes analyzing threshold transitions of optical density in individual scans within the plurality of scans.

6. The method of claim 1 wherein the reference optical density value is calculated with reference to a global or local signal-to-noise ratio.

7. The method of claim 1 wherein the reference optical density value is a mean, median, or maximum optical density value of any of:
 (a) an outer nuclear layer;
 (b) an inner segment and outer segment junction;
 (c) a retinal pigment epithelium;
 (d) a choroidal layer; or
 (e) a combination of any two or more of (a), (b), (c), or (d).

8. The method of claim 1 further comprising:
 presenting the texture analysis map to a user.

9. The method of claim 1 further comprising:
 detecting an abnormality of the inner retinal layer based on the texture analysis map.

10. The method of claim 1 further comprising:
 quantifying a degree of abnormality of the inner retinal layer based on the texture analysis map.

11. The method of claim 1 further comprising:
 converting the optical texture signature values $S_{xy}$ to a set of visual sensitivity values.

12. The method of claim 11 wherein converting the optical texture signature values $S_{xy}$ to a set of visual sensitivity values includes:
 applying a location-specific structure function association derived from linear or non-linear regression analysis between optical texture signature values and measured visual sensitivity.

13. The method of claim 1 further comprising:
 training a machine learning algorithm to detect an abnormality in the inner retinal layer based on the texture analysis map.

* * * * *